US007906124B2

(12) United States Patent
Laufer et al.

(10) Patent No.: US 7,906,124 B2
(45) Date of Patent: Mar. 15, 2011

(54) INACTIVATION OF SMOOTH MUSCLE TISSUE

(75) Inventors: Michael D. Laufer, Menlo Park, CA (US); David C. Auth, Kirkland, WA (US); Christopher J. Danek, San Carlos, CA (US); William J. Wizeman, Mountain View, CA (US); Gary S. Kaplan, San Francisco, CA (US)

(73) Assignee: Asthmatx, Inc., Sunnyvale, CA (US)

( * ) Notice: Subject to any disclaimer, the term of this patent is extended or adjusted under 35 U.S.C. 154(b) by 975 days.

(21) Appl. No.: 10/954,895

(22) Filed: Sep. 30, 2004

(65) Prior Publication Data

US 2006/0062808 A1 Mar. 23, 2006

Related U.S. Application Data

(60) Provisional application No. 60/610,925, filed on Sep. 18, 2004.

(51) Int. Cl.
*A61K 39/08* (2006.01)

(52) U.S. Cl. ............ 424/239.1; 424/9.1; 514/2; 514/12; 530/350

(58) Field of Classification Search .................. 424/9.1, 424/239.1; 514/2, 12; 530/350, 300
See application file for complete search history.

(56) References Cited

U.S. PATENT DOCUMENTS

| 5,437,291 | A | * | 8/1995 | Pasricha et al. ............... 128/898 |
| 5,728,094 | A | | 3/1998 | Edwards |
| 5,766,605 | A | * | 6/1998 | Sanders et al. ............. 424/239.1 |
| 5,972,026 | A | | 10/1999 | Laufer et al. |
| 5,976,175 | A | | 11/1999 | Hirano et al. |
| 6,003,517 | A | | 12/1999 | Sheffield et al. |
| 6,045,549 | A | | 4/2000 | Smethers et al. |
| 6,083,255 | A | | 7/2000 | Laufer et al. |
| 6,200,333 | B1 | | 3/2001 | Laufer |
| 6,273,907 | B1 | | 8/2001 | Laufer |
| 6,283,988 | B1 | | 9/2001 | Laufer et al. |
| 6,283,989 | B1 | | 9/2001 | Laufer et al. |
| 6,299,633 | B1 | | 10/2001 | Laufer |
| 6,411,852 | B1 | | 6/2002 | Danek et al. |
| 6,488,673 | B1 | | 12/2002 | Laufer et al. |
| 6,493,589 | B1 | | 12/2002 | Medhkour et al. |
| 6,634,363 | B1 | | 10/2003 | Danek et al. |
| 6,743,197 | B1 | | 6/2004 | Edwards |
| 6,767,544 | B2 | * | 7/2004 | Brooks et al. ............. 424/247.1 |
| 6,770,070 | B1 | | 8/2004 | Balbierz |
| 6,840,243 | B2 | | 1/2005 | Deem et al. |
| 6,974,579 | B2 | * | 12/2005 | Brin et al. .................. 424/239.1 |
| 7,027,869 | B2 | | 4/2006 | Danek et al. |
| 7,264,002 | B2 | | 9/2007 | Danek et al. |
| 7,273,055 | B2 | | 9/2007 | Danek et al. |
| 7,542,802 | B2 | | 6/2009 | Danek et al. |
| 7,556,624 | B2 | | 7/2009 | Laufer et al. |
| 7,740,017 | B2 | | 6/2010 | Danek et al. |
| 2004/0009180 | A1 | | 1/2004 | Donovan |
| 2004/0013692 | A1 | | 1/2004 | Aoki et al. |
| 2005/0010270 | A1 | | 1/2005 | Laufer |
| 2006/0062808 | A1 | * | 3/2006 | Laufer et al. ............... 424/239.1 |
| 2006/0137698 | A1 | | 6/2006 | Danek et al. |
| 2006/0254600 | A1 | | 11/2006 | Danek et al. |
| 2006/0278243 | A1 | | 12/2006 | Danek et al. |
| 2006/0278244 | A1 | | 12/2006 | Danek et al. |
| 2007/0083197 | A1 | | 4/2007 | Danek et al. |
| 2007/0102011 | A1 | | 5/2007 | Danek et al. |
| 2007/0106296 | A1 | | 5/2007 | Laufer et al. |
| 2007/0106348 | A1 | | 5/2007 | Laufer |
| 2007/0118190 | A1 | | 5/2007 | Danek et al. |
| 2008/0004596 | A1 | | 1/2008 | Yun et al. |
| 2009/0112203 | A1 | | 4/2009 | Danek et al. |
| 2009/0143705 | A1 | | 6/2009 | Danek et al. |
| 2009/0143776 | A1 | | 6/2009 | Danek et al. |
| 2009/0192508 | A1 | | 7/2009 | Laufer et al. |

FOREIGN PATENT DOCUMENTS

| WO | WO-9505842 | 3/1995 |
| WO | WO0062699 A3 | 10/2000 |

OTHER PUBLICATIONS

An, S.S et al., Airway smooth muscle dynamics: a common pathway of airway obstruction in asthma, European Respiratory Journal, 2007, vol. 29, No. 5, pp. 834-800.

Bel, E. H., Hot Stuff: Bronchial Thermoplasty for Asthma, American Journal of Respiratory and Critical Care Medicine, 2006, vol. 173, pp. 941-942.

Brown, R. H. et al., In vivo evaluation of the effectiveness of bronchial thermoplasty with computed tomography, Journal of Applied Physiology, 2005, vol. 98, pp. 1603-1606.

Brown, R. H. et al., Effect of bronchial thermoplasty on airway distensibility, European Respiratory Journal, vol. 26, No. 2, pp. 277-282.

Chhajed, P., Will There be a Role for Bronchoscopic Radiofrequency Ablation?, 2005, J Bronchol, vol. 12, No. 3, p. 184.

Cox, G., et al., Early Clinical Experience With Bronchial Thermoplasty for the Treatment of Asthma, 2002, p. 1068.

Cox, G. et al., Asthma Control During the Year After Bronchial Thermoplasty, The New England Journal of Medicine, Mar. 29, 2007, vol. 356, No. 13, pp. 21327-1337.

Cox, G. et al., Bronchial Thermoplasty: One-Year Update, American Thoracic Society Annual Meeting, 2004, p. 1.

Cox, G., et al., Development of a Novel Bronchoscopic Therapy for Asthma, Journal of Allergy and Clinical Immunology, 2003, p. 1.

(Continued)

*Primary Examiner* — Chih-Min Kam
(74) *Attorney, Agent, or Firm* — Perkins Coie LLP

(57) ABSTRACT

Treatment and procedures for treating bodily conduits involves deactivating, killing, or otherwise treating smooth muscle tissue of the conduit.

8 Claims, 3 Drawing Sheets

OTHER PUBLICATIONS

Cox, G., et al., Bronchial Thermoplasty for Asthma, American Journal of Respiratory and Critical Care Medicine, 2006, vol. 173, pp. 965-969.
Cox, G., et al., Bronchial Thermoplasty: Long-Term Follow-up and Patient Satisfaction, 2004, p. 1.
Cox, G., et al., Radiofrequency ablation of airway smooth muscle for sustained treatment of asthma: preliminary investigations, European Respiratory Journal, 2004, 24, pp. 659-663.
Cox, G., et al., Clinical Experience with Bronchial Thermoplasty for the Treatment of Asthma, 2003, Chest 124, p. 106S.
Cox, G., et al., Impact of bronchial thermoplasty on asthma status: interim results from the AIR trial, 2006. European Respiratory Society Annual Meeting. Munich, Germany, p. 1.
Danek, C. J., et al., Bronchial thermoplasty reduces canine airway responsiveness to local methacholine challenge, 2002, American Thoracic Society Annual Meeting, p. 1.
Danek, C. J., et al., Asthma Intervention Research (AIR) Trial Evaluating Bronchial Thermoplasty™: Early Results, 2002, American Thoracic Society Annual Meeting, p. 1.
Danek, C.J., et al., Reduction in airway hyperresponsiveness to methacholine by the application of RF energy in dogs, J. Appl Physiol, 2004, vol. 97, pp. 1946-1953.
Solway, J. at al., Airway Smooth Muscle as a Target for Asthma Therapy, The New England Journal of Medicine, Mar. 29, 2007, 356(13), pp. 1367-1369.
Laviolette, et al., Asthma Intervention Research (AIR) Trial: Early Safety Assessment of Bronchial Thermoplasty, 2004, p. 1.
Leff, et al., Bronchial Thermoplasty Alters Airway Smooth Muscle and Reduces Responsiveness in Responsiveness in Dogs: A Possible Procedure for the Treatment of Asthma, American Thoracic Society Annual Meeting, 2002, p. 1.
Lim, E. C. et al., Botulinum Toxin: A Novel Therapeutic Option for Bronchial Asthma?, Medical Hypotheses, 2006, vol. 66, pp. 915-919.
Lombard, et al., Histologic Effects of Bronchial Thermoplasty of Canine and Human Airways, American Thoracic Society Annual Meeting, 2002, p. 1.
Mayse, M. et al., Clinical Pearls for Bronchial Thermoplasty, J Bronchol, Apr. 2007, vol. 14, No. 2, pp. 115-123.
Miller, J. D. et al., A Prospective Feasibility Study of Bronchial Thermoplasty in the Human Airway, 2005, vol. 127, No. 6, pp. 1999-2006.
Miller, J. D. et al., Bronchial Thermoplasty is Well Tolerated by Non-Asthmatic Patients Requiring Lobectomy, 2002, American Thoracic Society Annual Meeting, p. 1.
Rubin, et al. Bronchial Thermoplasty Improves Asthma Status of Moderate to Severe Peristent Asthmatics Over and Above Current Standard-of-Care, 2006, American College of Chest Physicians, 2 pages.
Wilson, S. R. et al., Global assessment after bronchial thermoplasty: the patient's perspective, Journal of Outcomes Research, 2006, vol. 10, pp. 37-46.
Sterk, P. J., Heterogencity of Airway Hyperresponsiveness: Time for Unconventional, but Traditional Studies, 2004, The American Pshychological Society, pp. 2017-2018.
Toma, T. P., Brave New World for Interventional Bronchoscopy, 2005, Thorax, vol. 60, pp. 180-181.
Trow, T., Clinical Year in Review 1, proceedings of the American Thoracic Society, 2006, vol. 3, pp. 553-556.
Wizeman, et al., A Computer Model of Thermal Treatment of Airways by Radiofrequency (RF) Energy Delivery, 2007, American Thoracic Society Annual Meeting, p. 1.
Bakhai, et al., "Bronchial Artery Delivery Of Viral Vectors For Gene Delivery In Cystic Fibrosis; Superior To Airway Delivery?," BMC Pulmonary Medicine, Apr. 3, 2002, pp. 1-4, 2:2, available from http://www.biomedcentral.com/1471-2466/2/2.
Google search, Botox, Juvederm, Restylane, Artefill in Dallas. 2 pages, http://www.google.com/search?sourceid=navclient&aq=t&le=UTF-8&ris=GWYA,GWYA:2005-07,GWYA:en&q=botox+microsphere+size (Oct. 11, 2007).
Scheving, et al., "Microsphere Drug Delivery Systems," Chronobiotechnology and Chronobiological Engineering, 1987, pp. 56-58, ISBN 90-247-3471-1, Martinus Nijhoff Publishers.
Spencer, James M., "Chapter 2: Facial Anatomy and the Use of Botulinum Toxin," Botulinum Toxin in Clinical Dermatology, 2006, pp. 43-44, ISBN 1-842-14-2445, Taylor & Francis.
Campbell et al., 1999. Biology, Fifth Edition. ISBN 0-8053-6573-7, Benjamin/Cummings. Chapter 42, p. 822-823.
Davis, L.E., 1993. Botulinum Toxin From Poison to Medicine. West J Med., 158:25-29.
Raven, P.H. and Johnson G.B., 1992. Biology, Third Edition. ISBN 0-8016-6372-5, Mosby-Year Book, Inc. Chapter 51, p. 1060 and 1062-1063.
National Institute of Allergy and Infectious Diseases. Summary of the NIAID Expert Panel on Botulinum Toxins. Nov. 20, 2002. Available at (http://www.niaid.nih.gov/dmid/pdf/biotresearchagenda.pdf).
Co-pending U.S. Appl. No. 09/095,323, filed Jun. 10, 1998, Inventor Laufer et al.
Co-pending U.S. Appl. No. 12/727,156, filed Mar. 18, 2010, Inventor Danek et al.
Co-pending U.S. Appl. No. 12/765,704, filed Apr. 22, 2010 Inventor Danek et al.
NIH, National Heart, Lung, and Blood Institute Global Strategy for Asthma Management and Prevention, 2002, 192 Pages Total.
Janssen L. J., "Asthma therapy: how far have we come, why did we fail and where should we go next?," Eur Respir J, 2009, 33, pp. 11-20.
Kraft M., "The distal airways: are they Important in asthma?," European Respiratory, 1999, 1403-1417.
Peter K. Jeffery, "Remodeling in Asthma and Chronic Obstructive Lung Disease," American Journal of Respiratory and Critical Care Medicine, 2001, 164 (10), 13516.
Seow C.Y., et al., "Signal Transduction in Smooth Muscle Historical perspective on airway smooth muscle: the saga of a frustrated cell," J Appl Physiol, 2001, 91, 938-952.
Stephanie A.Shore, "Airway Smooth Muscle in Asthma—Not Just More of the Same," N Engl J Med, 2004, 351 (6), 531-532.
UNSW Embryo- Respiratory System [online], Embryology, 2007, [retrieved on Dec. 10, 2007], Retrieved from the Internet: (multiple references, many authors) (URL:http://embryology.med.unsw.edu.au/Refer/respire/sclect.htm).
Wayne Mitznerl, "Bronchial Thermoplasty in Asthma," Allergology International, 2006, 55, 225-234.

* cited by examiner

INACTIVATION OF SMOOTH MUSCLE TISSUE

CROSS-REFERENCE TO RELATED APPLICATIONS

This is a non-provisional of U.S. Provisional Application Ser. No. 60/610,925 filed Sep. 18, 2004, the entirety of which is incorporated by reference.

BACKGROUND OF THE INVENTION

Asthma is a serious chronic condition. In the United States alone, it is believed that asthma affects upward of 15 million Americans. Asthma is characterized by (i) bronchoconstriction, (ii) excessive mucus production, and (iii) inflammation and swelling of airways. These conditions cause widespread and variable airflow obstruction thereby making it difficult for the asthma sufferer to breathe. Asthma further includes acute episodes or attacks of additional airway narrowing via contraction of hyper-responsive airway smooth muscle. Other obstructive diseases such as COPD may also have a reversible component caused by one or more of the above mentioned three elements.

Asthma generally includes excessive mucus production in the bronchial tree. Usually, there is a general increase in bulk (hypertrophy) of the large bronchi and chronic inflammatory changes in the small airways. See for example, Hogg, J C. The Pathology of Asthma. *APMIS* 1997; 105:735-745. Excessive amounts of mucus are found in the airways and semisolid plugs of mucus may occlude some small bronchi. Also, the small airways are narrowed and may show inflammatory changes. See, e.g., Kraft M, *The Distal Airways: Are they Important in Asthma?* Eur Respir J 1999; 14:1403-1417. The reversible aspects of COPD include partial airway occlusion by excess secretions, bronchial wall edema, inflammation of the airways and airway narrowing as a result of smooth muscle contraction.

The role of airway smooth muscle and its effect in patients with asthma is gaining increased attention in the medical community. See, for example, Shore S, *Airway Smooth Muscle in Asthma—Not Just More of the Same,* 2004 N Engl J Med 351; 6; Jeffery P K. Remodeling in Asthma and Chronic Obstructive Lung Diseas., Am J. Respir Crit Care Med 2001; 1645: S28-S38; Global Initiative for Asthma (GINA) *Global Strategy for Asthma Management and Prevention,* NIH/NHLBI, 2002 NIH Publication No 02-3659 Furthermore, the literature tends to support the belief that smooth muscle tissue within the airways is not essential to normal lung physiology and that the smooth muscle tissue may in fact be a vestigial organ. In the case of individuals with asthma, the airway smooth muscle may actually cause medical complications. See, for example, Seow C Y, Fredberg J J, *Historical Perspective on Airway Smooth Muscle: the Saga of a Frustrated Cell,* 2001 J Appl Physiol 91(2):938-952; Mitzner W, *Airway Smooth Muscle: the Appendix of the Lung,* 2004 AJRCCM, 169:787-790.

Currently, asthma management includes a combination of stimulus avoidance and pharmacological mediation. Stimulus avoidance includes systematic identification of each type of stimuli and minimization of contact with each type of stimuli. It may, however, be impractical and not always helpful to avoid all potential stimuli.

Pharmacological mediation of asthma includes: (1) long term control through use of anti-inflammatories and long-acting bronchodilators and (2) short term management of acute exacerbations through use of short-acting bronchodilators. Both approaches require repeated and regular use of the prescribed drugs. High doses of corticosteroid anti-inflammatory drugs may include serious side effects requiring careful management. In addition, some patients are resistant to steroid treatment.

The difficulties involved in patient compliance with pharmacologic management and the difficulties of avoiding asthma triggering stimulus are common barriers to successful asthma management. It follows that current management techniques are neither completely successful nor free from side effects. Aside from the difficulties in these management techniques, some individuals may seek a more permanent solution to manage asthma.

Removal and/or deactivation of a body organ, vestigial or not, is medically acceptable as long as there is an overall benefit. A few examples of such procedures include removal of: body hair, the appendix, wisdom teeth, and portions of the cornea. Moreover, deactivation of certain muscles is accepted for cosmetic results. In this latter procedure, a physician injects botulism toxin type A (i.e., BOTOX®) directly into the corrugator and procerus muscles, preventing them from contracting and eventually causing the skin to become smoother.

Additionally, use of RF energy when applied to the airways has been shown to decrease the ability of smooth muscle tissue to narrow the airways. Danek C J, et al, Reduction in Airway Hyperresponsiveness to Methacholine by the Application of RF Energy in Dogs. 2004 J Appl Physiol. July 16 doi:10.1152/japplphysiol.01282.2003 (electronic publication—ahead of print)

In view of the foregoing, there remains an additional need for removal and/or deactivation of certain types of muscle which may contribute to or cause an impaired quality of life. In just one specific example, there remains a need to remove and/or deactivate certain airway smooth muscle to address the effects of certain pulmonary conditions, including but not limited to asthma.

BRIEF SUMMARY OF THE INVENTION

The present invention includes methods of treating smooth muscle tissue to prevent adverse effects resulting from constriction of body passages. Though the approaches discussed below discuss treatment of airway smooth muscle to prevent bronchoconstriction in cases of pulmonary disorders, it is contemplated that variations of the treatment are not limited to airway smooth muscle. Variations of the treatments and procedures described herein may be applied to non-airway smooth muscle where appropriate.

The treatments and procedures described below include methods of treating individual for hyper-responsiveness of a body passage, where the method comprises placing an agent into a blood vessel that supplies blood to tissue of the body passage, where the agent affects the ability of the body passage to constrict.

Also disclosed are methods of reducing the ability of a body passage to constrict in response to stimulus, where the method comprises altering a blood supply of smooth muscle tissue in the body passage to lessen or eliminate the ability of a portion of the smooth muscle tissue to constrict the body passage. In this case altering blood flow may include adding an agent to the blood that affects smooth muscle as discussed herein. Alternatively, or in combination, altering of the blood flow may comprise slowing or stopping the flow of blood to the target smooth muscle to affect the smooth muscle tissue.

The agents described herein may include toxins, radioactive agents, viral agents, and/or drugs. Example of such agents includes toxins such as natural, animal or insect toxins, or engineered toxins, I-131 (Iodine 131), laser absorptive dye, agents that bind to constituents of airway smooth muscle (e.g., myosin, actin), neutrophils, paralytic agents, embolizing agents, etc. Examples of agents that selectively affect smooth muscle tissue include: snake myotoxins; anti-bodies that bind to actin or myosin, with the impairment agent bound to the antibody. The agent may also include microspheres the size of the capillaries at the smooth muscle. These microspheres could also contain an additional agent.

Variations of the invention described herein include procedures and treatments that deliver a persistent treatment to prevent the ability of body passages to constrict.

DETAILED DESCRIPTION OF THE INVENTION

The invention relates to reducing or preventing a body passage from constricting by inactivating or therapeutically damaging the smooth muscle which causes contraction of the body passage. Although the invention described herein may have applications throughout the body, the variation of the invention described below relates to treating airway smooth muscle tissue to prevent or reduce constriction of the airways within a lung. As noted above, preventing or reducing constriction of the airways allows for improved breathing for individual suffering from a pulmonary condition, such as asthma.

The inventive treatment reduces the ability of the airways to constrict, narrow or to reduce in diameter due to airway smooth muscle contraction. The reduction in the ability of the smooth muscle to contract may be achieved by treating the smooth muscle itself or by treating other tissues to affect smooth muscle contraction or the response of the airway to the smooth muscle contraction. Treatment may also reduce airway responsiveness or the tendency of the airway to narrow or to constrict in response to a stimulus.

The reduction in smooth muscle and surrounding tissue may also have the added potential benefit of increasing the caliber or diameter of the airways, this benefit reduces the resistance to airflow through the airways. In addition to the use of debulking smooth muscle tissue to open up the airways, the devices and/or approach of the present invention may eliminate smooth muscle altogether by damaging or destroying the muscle.

In the airways, the smooth muscle is arranged externally to an airway in a generally helical pattern with pitch angles ranging from about −30 to about +30 degrees. Thus, the treatment of the smooth muscle, which may be selectively given in an appropriate pattern, interrupts or cuts through the helical pattern at a proper pitch and prevents the airway from constricting. Therefore, a variation of the invention may include treating the airway smooth muscle in one or more sites or in a pattern to eliminates contraction of the airways without completely eradicating smooth muscle and other airway tissue. Alternatively, a variation of the invention includes treating at one or a few sites to inactivate all or a significant portion of the airway smooth muscle.

Figure 1:
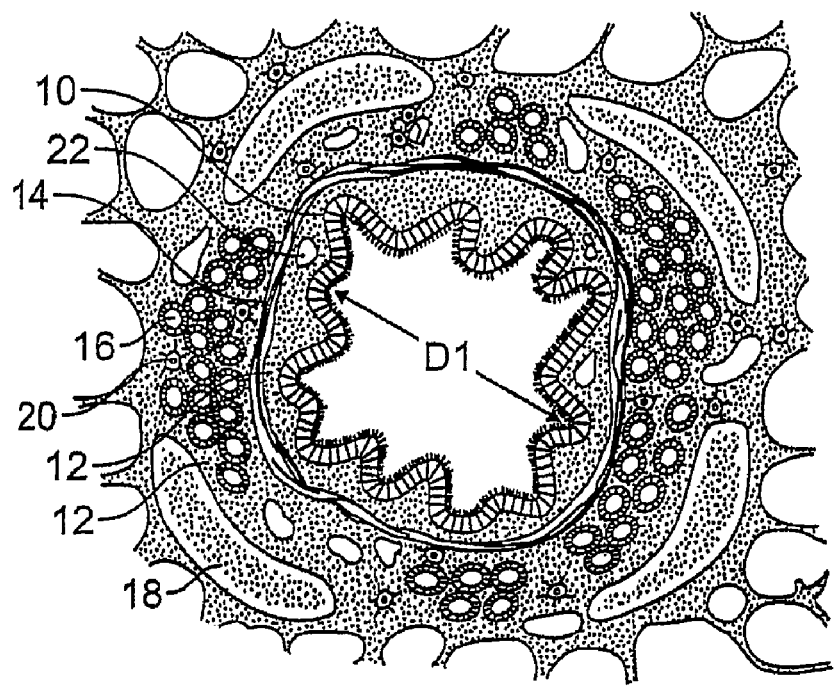
FIG. 1. is a cross sectional view of an airway in a healthy lung.
Figure 2:
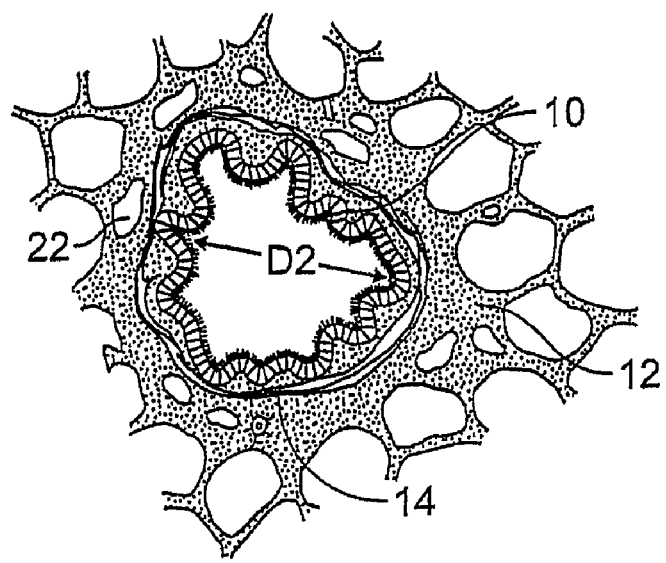
FIG. 2. shows a section through a bronchiole having an airway diameter smaller than that shown in FIG. 1.

FIGS. 1 and 2 illustrate cross sections of an airway and a bronchiole, respectively, in a healthy patient. The airway of FIG. 1 is a medium sized bronchus having an airway diameter D1 of about 3 mm. FIG. 2 shows a section through a bronchiole having an airway diameter D2 of about 1.5 mm. Each airway includes a folded inner surface or epithelium 10 surrounded by stroma 12 and smooth muscle tissue 14. The larger airways including the bronchus shown in FIG. 1 also have mucous glands 16 and cartilage 18 surrounding the smooth muscle tissue 14. Nerve fibers 20 and blood vessels 22 also surround the airway.

Figure 3:
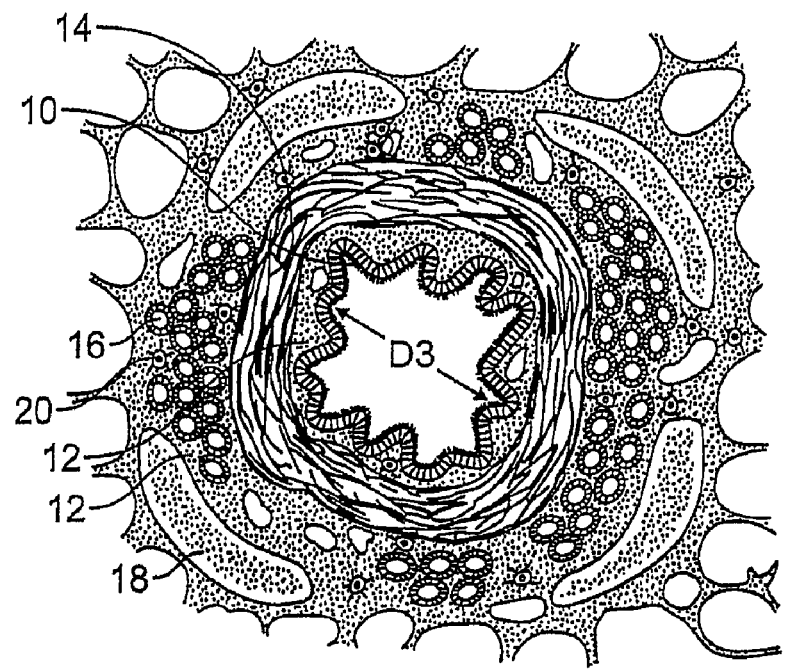
FIG. 3 illustrates an airway similar to that of FIG. 1 but in which the smooth muscle hypertrophied and increased in thickness causing reduction of the airway diameter.

FIG. 3 illustrates the bronchus of FIG. 1 in which the smooth muscle 14 hypertrophied and increased in thickness causing the airway diameter to be reduced from the diameter D1 to a diameter D3.

In any case, the smooth muscle tissue 14 is responsible for constriction of the airways. As noted herein, the adverse affects of excessive airway constriction may be alleviated by directly inactivating or deactivating the function of the airway smooth muscle.

The airway smooth muscle relies upon the bronchial vasculature for its blood supply. Therefore, any altering of the blood supply in the bronchial system significantly affects the airway smooth muscle as compared to the remaining airway wall or bronchial tissue. Because of this, the airway smooth muscle's blood supply may be treated so that the effects of the treatment are acceptably limited to the airway smooth muscle. Furthermore, the blood-air exchange function of the alveoli (the most distal portion of the airway that provides a gas exchange function), relies upon a separate vasculature network. So any actions taken on the bronchial vasculature may be controlled so that they will have little or no effect upon the remaining circulatory system, including the pulmonary vasculature.

Figure 4:
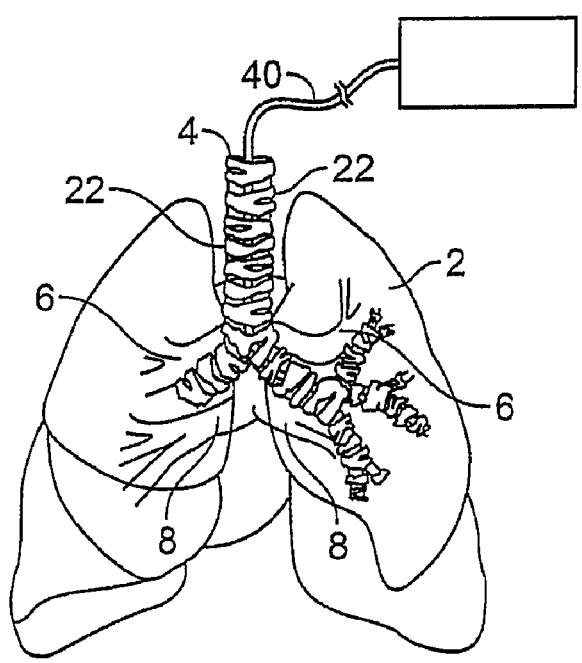
FIG. 4 is a representation of the lungs, airway, pulmonary vessels and bronchial vessels.

FIG. 4 is a representative illustration of the lungs 2, airways 4, pulmonary arteries 6, pulmonary veins 8, and bronchial veins and arteries 22. To deliver the treatment in accordance with the teachings described herein, a treatment location is selected. Generally, the bronchial arteries 22 run within the airway wall. It is noted that the location or treatment site may be selected either from sensing within the airway 4 (e.g., via Doppler sensing), external means by any mode of non-invasive detection, and/or by any other means of locating an acceptable site to provide the treatment.

FIG. 4 also illustrates a variation of the treatment where a catheter 40 advances into the airways. The catheter 40 may be equipped to perform the procedure as discussed herein. By advancing the catheter 40 through the airways, the treatment may be delivered to the bronchial artery without having to puncture the pleura.

Figure 5:
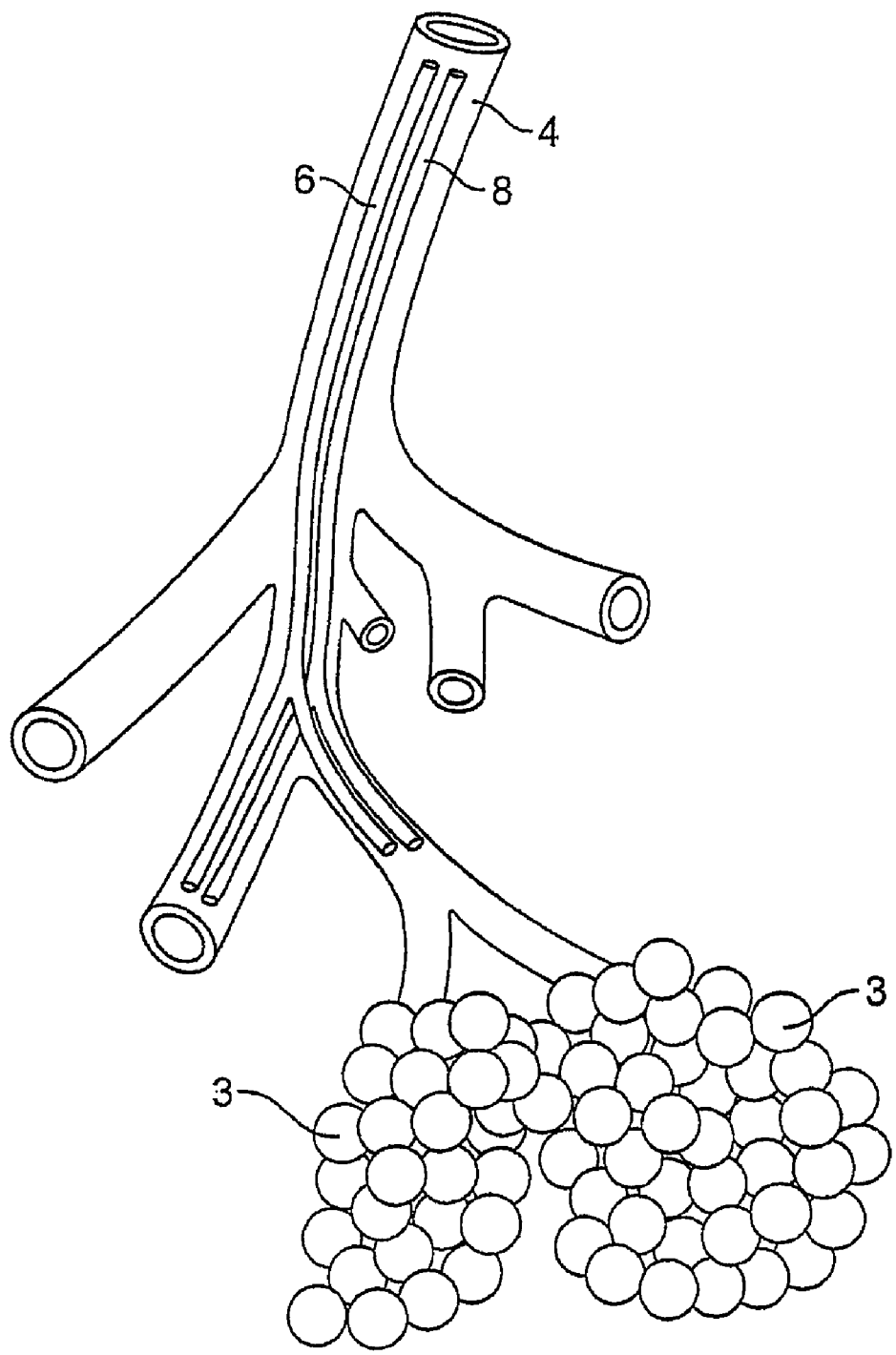
FIG. 5 is a representation of the bronchial artery and vein as it runs along an airway.

FIG. 5 shows a representation of an airway 4 terminating into the alveolus 3. As shown, the airway 4 includes a bronchial artery 6 and a bronchial vein 8 running exterior to the lumen of the airway. As illustrated, the bronchial arteries and veins 6 and 8 run externally along either side of the main bronchus and follow the branching of the airways 4. The location of the bronchial artery 6 allows for any number of modes of detection (e.g., Doppler, thermal, etc.) to locate a possible treatment site.

The treatment described herein may be provided via a minimally invasive approach. For example, a medical practitioner advances a treatment device 40 (e.g., a bronchoscope carrying a catheter, a catheter, etc.) into the airways 4. Alternatively, or in combination, the medical practitioner may apply the treatment from outside the body through injection, or even oral administration. Some variations of the treatment described herein allow for treatment of the airway smooth muscle tissue, which is located in a considerable number of airways, could be applied in a single or relatively few locations (e.g., one or more sites in the bronchial arteries.) This advantage allows for treatment at relatively few sites as opposed to having to treat the entire (or considerable portion) of the bronchial network.

In one variation of the treatment, the medical practitioner injects an agent into the bronchial artery or arteries 6 supplying the airways 4. As noted above, the agent affects the blood supplied to the smooth muscle tissue within the airway. In turn, the agent reaches the smooth muscle tissue to deactivate, kill or impair the function of the smooth muscle tissue. As a result, the inability of the smooth muscle tissue to constrict the airways improves the breathing condition of the patent (e.g., in cases of an asthma attack.)

The agents described herein may include toxins, radioactive agents, viral agents, and/or drugs. Example of such agents includes toxins such as natural, animal or insect toxins, or engineered toxins, I-131 (Iodine 131), laser absorptive dye, agents that bind to constituents of airway smooth muscle (e.g., myosin, actin), neutrophils, paralytic agents, embolizing agents, etc. Examples of agents that selectively affect smooth muscle tissue include: snake myotoxins; anti-bodies that bind to actin or myosin, with the impairment agent bound to the antibody. The agent may also include microspheres the size of the capillaries at the smooth muscle. These microspheres could also contain an additional agent.

A variation of the treatment may include delivering a second agent which counteracts the effect of the first agent. In such a case, the second agent is provided so that the treatment is limited to the desired part of the body (e.g., the airways.) For example, if a toxin is applied to the bronchial artery, a counteracting agent may be introduced systemically or locally but in a way so that the initial treatment is not rendered ineffective. For example, if the agent is cyanide the counteragent or protectant agent could be amyl nitrate Accordingly, as the agent affect the smooth muscle in the airways, the counteracting agent minimizes adverse effect on other smooth muscle that is not a subject of the treatment. Examples of such counteragents include, but is not limited to, antivenom. It is also contemplated that instead of a counteragent, a mechanical filter or binding substance may be used to collect or deactivate the agent before the agent is able to affect non-target tissues. Furthermore, a counteractive measure may be applied to the same effect as a counter agent. For example, an agent may be applied where the agent may be rendered ineffective under certain environments (e.g., upon the application of current, an electric field, or other chemical reaction.)

The counteragent may be provided in such a way that it allows for "dosing" of the agent. For example, the agent may be applied in a concentration strong enough to have the desired effect, but through dilution, degradation, or through systemic counteragent (at a dose that cannot protect the targeted tissues which see a "too strong" dose of agent) cannot affect other organ systems.

A variation of the treatment described herein includes ligating or reducing flow within the bronchial vessel or vessels so that the agent is trapped or delayed in the desired treatment location until a significant amount of the agent is absorbed or until the agent decays or is rendered inactive. For example, a radioactive agent with a properly selected half-life may be used. In this case, reducing the flow of the agent trapping the agent within the bronchial vessels may allow a sufficient amount of time to pass so that the radioactive agent decays sufficiently so that any of the agent that passes to other portions of the body is rendered sufficiently ineffective to cause any concern of side effects. This approach of reducing the blood flow may be accomplished at the arterial side of the flow (i.e., the inflow side), and/or may be accomplished at the venous side of the flow (i.e., the outflow side).

In another example of the inventive treatment, the blood supply to the target smooth muscle may be interrupted or reduced to starve the smooth muscle by reducing oxygen supply to the muscle to induce temporary or permanent deactivation of the muscle. In this variation of the treatment, the blood supply may be altered by introducing an agent that occludes blood flow in the vessel. In some cases, the blood vessels may be starved of necessary nutrients or otherwise induced to create damaging toxins on their own. The occluding agent could be any agent, combination of agents and/or devices that restricts blood flow.

Alternatively, or in addition, the blood supply may be altered by simply damaging the blood vessel or shunting blood flow to a different region so that blood does not reach the targeted smooth muscle tissue. For example, the bronchial artery may be coagulated to stop flow. In another variation, the blood flow in the bronchial artery may be shunted to the pulmonary vessels or the bronchial vein. The bronchial vein may also be closed to accomplish the appropriate result of affecting the smooth muscle tissue.

The treatment described herein may be combined with other conventional treatments. For example, for asthma management, the treatments herein may be combined with stimulus avoidance or pharmacological management of asthma. In addition, the treatments may be combined with the treatments described in the following commonly assigned patents and applications. U.S. patent applications: 09/095,323 filed Jun. 10, 1998; 09/436,455 filed Nov. 8, 1999. U.S. Published application: 20030233099A1; 20040010289A1; 20020091379A1. U.S. Pat. Nos. 6,411,852; 6,634,363 the entirety of all of which are incorporated by reference herein so that they may be combined with the inventive procedures and treatments described herein.

The effectiveness of the treatments and procedures described above may be further improved through exercise or activation of the target smooth muscle while the treatment or procedure is in process. For example, the smooth muscle may be stimulated during treatment to increase its demand for oxygen from the blood system. In turn, the increased demand for oxygen may cause, either more of the agent to pass to the target smooth muscle, or in cases where the blood flow is interrupted, the lack of oxygen causes ischemia of the "activated" smooth muscle at an increased rate.

In addition, the effectiveness of the treatments and procedures described herein may be titrated. In this case, the treatment may be performed under stimulated constriction of the airways. A medical practitioner would then observe the effects of the treatment (either real time and/or under direct observation, or through other measurement modes). Upon reaching the desired effect, the medical practitioner would stop the treatment. For example, methocholine, which stimulates smooth muscle activity, may be placed in the airway to stimulate the smooth muscle. Alternatively, or in combination, the smooth muscle may be stimulated electrically, or by other stimulus.

The treatments and/or agents described herein may also be combined with temperature, dyes, or other detectible additives. For example, blood on the arterial side of the airway smooth muscle may be heated or cooled (alternatively, it may be the agent that is heated or cooled.) Then, by measuring the blood flow on the venous side of the airway smooth muscle, one is able to confirm when the agent or effect has passed through the smooth muscle. For example, one variation of the invention includes cooling the agent, injecting the agent into the blood flow, then measuring the temperature of the vein or venous flow. A drop in temperature (or observation of the additive) at this location informs the medical practitioner that the agent or altered blood passed through the smooth muscle.

While the invention has been described in detail with reference to the preferred embodiments thereof, it will be apparent to one skilled in the art that various changes and modifications can be made and equivalents employed, without departing from the present invention. Furthermore, the above illustrations and descriptions are examples of a number of non-exhaustive variations the invention described herein. It is contemplated that combinations of aspects of specific embodiments or combinations of the specific embodiments themselves are within the scope of this disclosure.

We claim:

1. A method of treating asthma, the method comprising:
    locating a blood vessel supplying airway smooth muscle in a lung; and
    injecting botulinum toxin type A into the blood vessel in an amount effective to lessen airway smooth muscle contraction.

2. The method of claim 1, where the blood vessel comprises a bronchial artery.

3. The method of claim 1, further selecting a second vascular site, and reducing a blood flow within the second vascular site to decrease a flow rate of the toxin in the blood vessel.

4. The method of claim 1, where the toxin blocks flow of blood within the blood vessel to damage smooth muscle.

5. The method of claim 1, further comprising stimulating an airway in the lung.

6. The method of claim 1, where stimulating the airway increases absorption of the toxin.

7. The method of claim 1, further comprising monitoring blood supply to determine an amount of the toxin remaining in the blood supply.

8. The method of claim 1, where the toxin irreversibly damages smooth muscle tissue.

* * * * *

UNITED STATES PATENT AND TRADEMARK OFFICE
CERTIFICATE OF CORRECTION

PATENT NO. : 7,906,124 B2  
APPLICATION NO. : 10/954895  
DATED : March 15, 2011  
INVENTOR(S) : Michael D. Laufer et al.

It is certified that error appears in the above-identified patent and that said Letters Patent is hereby corrected as shown below:

ON THE TITLE PAGE: ITEM (56) REFERENCES CITED:

On page 2, in column 1, under "Other Publications", line 46, delete "Peristent" and insert -- Persistent --, therefor.

On page 2, in column 1, under "Other Publications", line 52, delete "Heterogencity" and insert -- Heterogeneity --, therefor.

On page 2, in column 1, under "Other Publications", line 54, delete "Pshychological" and insert -- Psychological --, therefor.

IN THE SPECIFICATIONS:

In column 3, line 5, delete "myotoxins;" and insert -- mycotoxins; --, therefor.

In column 3, line 8-9, delete "micropspheres" and insert -- microspheres --, therefor, In column 5, line 27, delete "myotoxins;" and insert -- mycotoxins: --, therefor.

In column 5, line 30-31, delete "micropspheres" and insert -- microspheres --, therefor.

IN THE CLAIMS:

In column 8, line 14, in claim 6, delete "claim 1," and insert -- claim 5, --, therefor.

Signed and Sealed this  
Seventh Day of June, 2011

David J. Kappos  
*Director of the United States Patent and Trademark Office*